(12) United States Patent
Koka et al.

(10) Patent No.: US 9,993,644 B2
(45) Date of Patent: Jun. 12, 2018

(54) SYSTEMS AND METHODS FOR FITTING AN ELECTRO-ACOUSTIC STIMULATION SYSTEM TO A PATIENT

(71) Applicant: ADVANCED BIONICS AG, Staefa (CH)

(72) Inventors: Kanthaiah Koka, Valencia, CA (US); Leonid M. Litvak, Los Angeles, CA (US); Abhijit Kulkarni, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 0 days. days.

(21) Appl. No.: 15/516,367

(22) PCT Filed: Oct. 6, 2014

(86) PCT No.: PCT/US2014/059342
§ 371 (c)(1),
(2) Date: Mar. 31, 2017

(87) PCT Pub. No.: WO2016/057018
PCT Pub. Date: Apr. 14, 2016

(65) Prior Publication Data
US 2017/0239475 A1    Aug. 24, 2017

(51) Int. Cl.
*A61N 1/36* (2006.01)
*A61N 1/05* (2006.01)
*H04R 25/00* (2006.01)

(52) U.S. Cl.
CPC ....... *A61N 1/36032* (2013.01); *A61N 1/0541* (2013.01); *H04R 25/606* (2013.01); *H04R 25/70* (2013.01)

(58) Field of Classification Search
CPC .... A61N 1/0541; A61N 1/36; A61N 1/36032; H04R 25/606; H04R 25/70
(Continued)

(56) References Cited

U.S. PATENT DOCUMENTS 8,086,319 B2    12/2011  van Dijk
8,170,678 B2 *   5/2012  Polak ................ A61B 5/121
                                                 607/57

(Continued)

FOREIGN PATENT DOCUMENTS

WO    WO 2012/056427      5/2012
WO    WO 2013/142843      9/2013
WO    WO-2017182931 A1   10/2017

OTHER PUBLICATIONS

Miller, et al., "Auditory Nerve Fiber Responses to Combined Acoustic and Electric Stimulation", *Journal of the Association for Research in Otolaryngology*, Springer-Verlag, NE, vol. 10, No. 3, Feb. 10, 2009, pp. 425-445.

(Continued)

*Primary Examiner* — Christopher A Flory
(74) *Attorney, Agent, or Firm* — ALG Intellectual Property, LLC

(57) ABSTRACT

An exemplary fitting system 1) directs an EAS system to concurrently apply acoustic stimulation to a patient by way of a loudspeaker and electrical stimulation to the patient by way of an electrode located within a cochlea of the patient, 2) determines an interactive effect that the electrical stimulation has on the acoustic stimulation, 3) directs, if the fitting facility determines that the interactive effect is suppressive, the EAS system to use a first stimulation strategy that steers a current field produced by stimulation of the electrode away from intracochlear acoustic responders within the patient that are associated with the acoustic stimulation, and 4) directs, if the fitting facility does not determine that the interactive effect is suppressive, the EAS system to use a second stimulation strategy that steers the current field produced by the stimulation of the electrode towards the intracochlear acoustic responders.

20 Claims, 12 Drawing Sheets

(58) Field of Classification Search
USPC .......................................................... 607/57
See application file for complete search history.

(56) References Cited

U.S. PATENT DOCUMENTS

| | | | | |
|---|---|---|---|---|
| 8,233,651 | B1* | 7/2012 | Haller | A61N 1/36036 381/318 |
| 8,280,087 | B1* | 10/2012 | Bacon | H04R 25/353 381/312 |
| 8,437,859 | B1* | 5/2013 | Haller | A61N 1/36032 607/55 |
| 8,699,734 | B1* | 4/2014 | Haller | A61N 1/36036 381/318 |
| 9,008,339 | B1* | 4/2015 | Bacon | H04R 25/353 381/312 |
| 9,061,149 | B2* | 6/2015 | Menzl | H04R 25/70 |
| 2005/0105741 | A1* | 5/2005 | Niederdrank | H04R 25/70 381/60 |
| 2005/0261748 | A1 | 11/2005 | van Dijk | |
| 2006/0276854 | A1* | 12/2006 | Shalev | A61N 1/0546 607/45 |
| 2008/0234793 | A1* | 9/2008 | Gibson | A61N 1/0541 607/137 |
| 2009/0254149 | A1* | 10/2009 | Polak | A61B 5/121 607/57 |
| 2010/0030012 | A1* | 2/2010 | Meskens | A61N 1/36032 600/25 |
| 2010/0131032 | A1* | 5/2010 | Oberhofer | A61B 5/121 607/57 |
| 2010/0145411 | A1* | 6/2010 | Spitzer | A61N 1/36032 607/57 |
| 2010/0152814 | A1* | 6/2010 | Polak | A61B 5/04001 607/57 |
| 2011/0066210 | A1* | 3/2011 | Wilson | A61N 1/36032 607/57 |
| 2011/0166627 | A1* | 7/2011 | Carter | A61N 1/0541 607/57 |
| 2012/0143283 | A1* | 6/2012 | Polak | A61B 5/121 607/57 |
| 2012/0277835 | A1* | 11/2012 | Della Santina | A61N 1/0526 607/62 |
| 2013/0006328 | A1 | 1/2013 | Bouchataoui et al. | |
| 2013/0116746 | A1* | 5/2013 | Polak | H04R 25/353 607/57 |
| 2013/0267767 | A1* | 10/2013 | Polak | H04R 25/70 600/25 |
| 2013/0345767 | A1* | 12/2013 | Menzl | H04R 25/70 607/3 |
| 2015/0012053 | A1* | 1/2015 | Downing | A61N 1/0541 607/3 |
| 2015/0049890 | A1* | 2/2015 | Agrawal | A61B 5/04001 381/314 |
| 2015/0051654 | A1* | 2/2015 | Litvak | A61B 5/04001 607/3 |
| 2015/0057714 | A1* | 2/2015 | Litvak | A61B 5/04001 607/3 |
| 2015/0209580 | A1* | 7/2015 | Della Santina | A61N 1/36032 607/66 |
| 2015/0271612 | A1* | 9/2015 | Menzl | H04R 25/70 607/3 |
| 2015/0334496 | A1* | 11/2015 | Menzl | H04R 25/70 607/3 |
| 2015/0341731 | A1* | 11/2015 | Polak | H04R 25/70 600/25 |
| 2016/0235986 | A1* | 8/2016 | Murad | A61N 1/36032 |
| 2016/0243361 | A1* | 8/2016 | Litvak | A61B 5/125 |
| 2016/0331954 | A1* | 11/2016 | Gibson | A61N 1/0541 |

OTHER PUBLICATIONS

Lin, et al., "Ipsilateral Masking Between Acoustic and Electric Stimulations", *The Journal of the Acoustical Society of America*, American Institute of Physics for the Acoustical Society of America, New York, NY, vol. 130, No. 2, Aug. 1, 2011, pp. 858-865.
International Search Report and Written Opinion received in International Application No. PCT/US14/059342, dated Apr. 28, 2015.

* cited by examiner

SYSTEMS AND METHODS FOR FITTING AN ELECTRO-ACOUSTIC STIMULATION SYSTEM TO A PATIENT

BACKGROUND INFORMATION

Many hearing loss patients have some degree of residual hearing in the low frequencies (e.g., below 1 kHz) and a severe hearing loss in the high frequencies (e.g., above 1 kHz). These people cannot benefit from traditional hearing aid amplification because of the severity of the hearing loss in the high frequencies. Nor are they classic cochlear implant candidates, because of their mostly intact low frequency residual hearing.

For this group of people, electro-acoustic stimulation ("EAS") systems have been developed that provide such patients with the ability to perceive both low and high frequencies. Electro-acoustic stimulation combines the functionality of a hearing aid and a cochlear implant together in the same ear by providing acoustic stimulation representative of low frequency audio content and electrical stimulation representative of high frequency content. The auditory nerve combines the acoustic and electric stimuli into one auditory signal. Results of various studies have shown that electro-acoustic stimulation may enhance speech understanding, pitch discrimination, and music appreciation.

Unfortunately, the acoustic and electrical stimulation provided by an EAS system may sometimes negatively interact with each other, thereby degrading the listening experience of an EAS patient. For example, the electrical stimulation provided by an EAS system may have a suppressive effect on the acoustic stimulation provided by the EAS system (e.g., by preventing the neurons in the apical region of the cochlea from responding to the acoustic stimulation).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for fitting an electro-acoustic stimulation ("EAS") system to a patient are described herein. As will be described below, a fitting system may 1) direct, during a fitting session, an EAS system to concurrently apply acoustic stimulation to a patient by way of a loudspeaker and electrical stimulation to the patient by way of an electrode located within a cochlea of the patient, 2) determine an interactive effect that the electrical stimulation has on the acoustic stimulation, 3) direct, if the determined interactive effect is suppressive, the EAS system to use, during a stimulation session subsequent to the fitting session, a first stimulation strategy that steers a current field produced by stimulation of the electrode away from intracochlear acoustic responders within the patient that are associated with the acoustic stimulation, and 4) direct, if the determined interactive effect is enhancing, the EAS system to use, during the stimulation session subsequent to the fitting session, a second stimulation strategy that steers the current field produced by the stimulation of the electrode towards the intracochlear acoustic responders. As used herein, "acoustic responders" refer to portions of the cochlea (e.g., auditory nerve tissue) that respond to acoustic stimulation (e.g., by producing an evoked response in response to the acoustic stimulation).

By directing the EAS system to steer the current field produced by stimulation of the electrode away from the intracochlear acoustic responders associated with the acoustic stimulation if the determined interactive effect is suppressive, the systems and methods described herein may reduce the suppressive interactive effect that stimulation of the electrode may have on acoustic stimulation applied during the stimulation session. Likewise, by directing the EAS system to steer the current field produced by stimulation of the electrode towards the intracochlear acoustic responders associated with the acoustic stimulation if the interactive effect is enhancing, the systems and methods described herein may enhance the acoustic stimulation applied during the stimulation session.

Moreover, as will be described below, the methods and systems described herein may facilitate an objective determination of an interactive effect that electrical stimulation has on acoustic stimulation and vice versa. As such, the methods and systems may be used to fit EAS systems to adults as well as to children and other types of patients who have difficulty providing subjective feedback during a fitting session. The methods and systems described herein may also determine (and/or aid a clinician in determining) various EAS parameters such as, but not limited to, crossover frequencies, intensity levels at the crossover frequencies, slopes of filters at the crossover frequencies, and/or other EAS parameters used to fit an EAS system to a patient.

Figure 1:
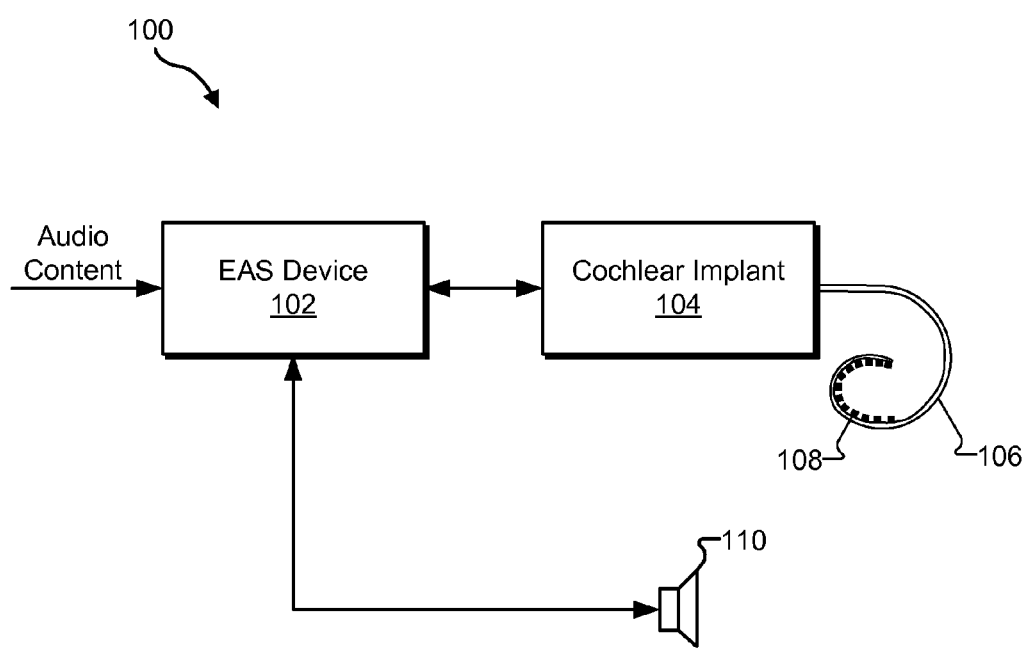
FIG. 1 illustrates an exemplary electro-acoustic stimulation ("EAS") system according to principles described herein.

FIG. 1 illustrates an exemplary EAS system 100. As shown, EAS system 100 may include an EAS device 102, a cochlear implant 104, an electrode array 106 having a plurality of electrodes 108 disposed thereon, and a loudspeaker 110 (also referred to as a receiver).

EAS device 102 may include any suitable device (e.g., sound processor) configured to process audio content (e.g., one or more audio signals) presented to a patient and provide electrical and/or acoustic stimulation representative of the audio signals to the patient. In some examples, EAS device 102 may be implemented by an externally worn unit (e.g., a behind-the-ear device, a body worn device, etc.).

As mentioned, EAS device 102 may be used when the patient has some residual some hearing in the low frequencies (e.g., below 1000 Hz) and severe hearing loss in the high frequencies (e.g., above 1000 Hz). To this end, EAS device 102 may, in some embodiments, direct cochlear implant 104 to apply electrical stimulation representative of audio content included in a relatively high frequency band (e.g., above 1000 Hz) to one or more stimulation sites within the patient by way of one or more of electrodes 108 and loudspeaker 110 to apply acoustic stimulation representative of audio content included in a relatively low frequency band (e.g., below 1000 Hz) to the patient.

Cochlear implant 104 may include any suitable auditory prosthesis configured to be at least partially implanted within a patient as may serve a particular implementation. For example, cochlear implant 104 may include an implantable cochlear stimulator, a brainstem implant and/or any other type of auditory prosthesis. EAS device 102 and cochlear implant 104 may communicate by way of any suitable wired or wireless communication channel.

Electrode array 106 may be implanted within the patient such that electrodes 108 are in communication with stimulation sites within the cochlea. In this configuration, EAS device 102 may direct cochlear implant 104 to apply electrical stimulation representative of an audio signal to one or more stimulation sites within the patient by way of one or more of electrodes 108. As used herein, the term "in communication with" refers to electrodes 108 being adjacent to, in the general vicinity of, in close proximity to, directly next to, or directly on the one or more stimulation sites. Any number of electrodes 108 (e.g., sixteen) may be disposed on electrode array 106 as may serve a particular implementation.

Figure 2:
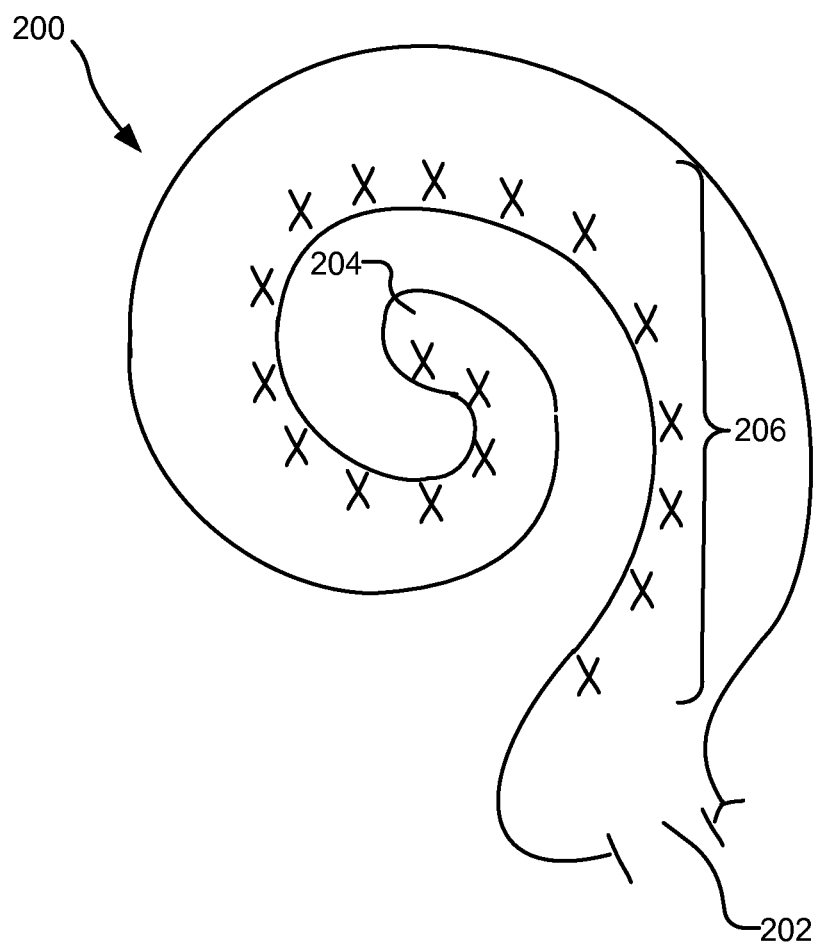
FIG. 2 illustrates a schematic structure of the human cochlea.

FIG. 2 illustrates a schematic structure of the human cochlea 200 into which electrode array 106 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode array may vary depending on the insertion depth of the electrode array, the anatomy of the patient's cochlea, and/or any other factor as may serve a particular implementation.

Once a patient has been implanted with EAS system 100, and during follow-up test and checkups thereafter, it may be necessary to fit EAS system 100 to the patient. Such "fitting" may include setting and/or adjustment of one or more control parameters governing an operation of EAS system 100. To facilitate fitting of EAS system 100 to a patient, a fitting system may be selectively and communicatively coupled to EAS system 100. As will be described below, the fitting system may additionally or alternatively be implemented by EAS device 102.

Figure 3:
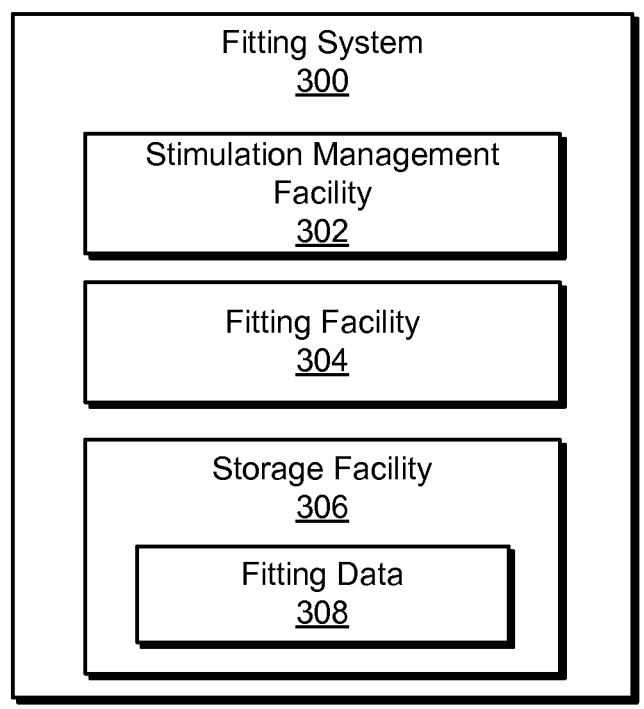
FIG. 3 illustrates an exemplary fitting system according to principles described herein.

FIG. 3 illustrates an exemplary fitting system 300. As shown in FIG. 3, fitting system 300 may include a stimulation management facility 302, a fitting facility 304, and a storage facility 306, which may be in communication with one another using any suitable communication technologies. One or more of facilities 302-306 may include one or more computing devices and/or processors that perform one or more of the functions described herein. Facilities 302-306 will now be described in more detail.

Storage facility 306 may maintain fitting data 308 generated and/or utilized by stimulation management facility 302 and/or fitting facility 304. Storage facility 306 may be configured to maintain additional or alternative data as may serve a particular implementation.

Stimulation management facility 302 may perform one or more acoustic and/or electrical stimulation management operations. For example, stimulation management facility 302 may direct, during a fitting session, an EAS system (e.g., EAS system 100) to concurrently apply acoustic stimulation to a patient by way of a loudspeaker (e.g., loudspeaker 110 or any other suitable transducer, headphone, earphone, and/or specialized hearing aid) and electrical stimulation to the patient by way of an electrode (e.g., one of electrodes 108) located within a cochlea of the patient. As used herein, a "fitting session" refers to a period of time during which one or more fitting operations are performed. The acoustic and electrical stimulation may have any suitable characteristic as may serve a particular implementation. For example, the acoustic stimulation may include a relatively low frequency tone burst (e.g., a 125 Hz tone burst) and the electrical stimulation may include monopolar stimulation (e.g., a pulse train). The electrode to which the electrical stimulation is applied may be any electrode located within the cochlea of the patient (e.g., the most apical electrode).

Fitting facility 304 may perform one or more fitting operations associated with an EAS system (e.g., EAS system 100). For example, fitting facility 304 may detect an interaction between the acoustic stimulation and the electrical stimulation applied by an EAS system at the direction of stimulation management facility 302. Fitting facility 304 may then set one or more control parameters governing an operation of the EAS system based on the detected interaction. Various examples of detecting an interaction between acoustic and electrical stimulation and then setting one or more control parameters governing an operation of an EAS system based on the detected interaction will now be described.

In some examples, fitting facility 304 may determine an interactive effect that the electrical stimulation has on the acoustic stimulation and set one or more electrical stimulation control parameters governing an operation of the EAS system based on the determined interactive effect. As used herein, "electrical stimulation control parameters" refer to control parameters that govern a manner in which an EAS system applies electrical stimulation by way of one or more electrodes disposed within a cochlea of a patient.

Fitting facility 304 may determine an interactive effect that the electrical stimulation has on the acoustic stimulation in any suitable manner. To illustrate, fitting facility 304 may determine an interactive effect that the electrical stimulation has on the acoustic stimulation by measuring an evoked response that occurs in response to the concurrent application of the acoustic stimulation and the electrical stimulation and comparing the evoked response to a baseline response that occurs in response to an application of the acoustic stimulation by itself. As used herein, an "evoked response" refers to an intracochlear hair-cell response (i.e., cochlear microphonics), a neural response (e.g., an auditory nerve response, a brainstem response, a compound action potential), an electrocochlear potential ("ECoG"), and/or any other type of neural or physiological response that may occur within a patient in response to application of acoustic and/or electrical stimulation to the patient. A "baseline response" refers to an evoked response that occurs in response to application of a single type of stimulus (e.g., acoustic stimulation only).

Figure 4A:
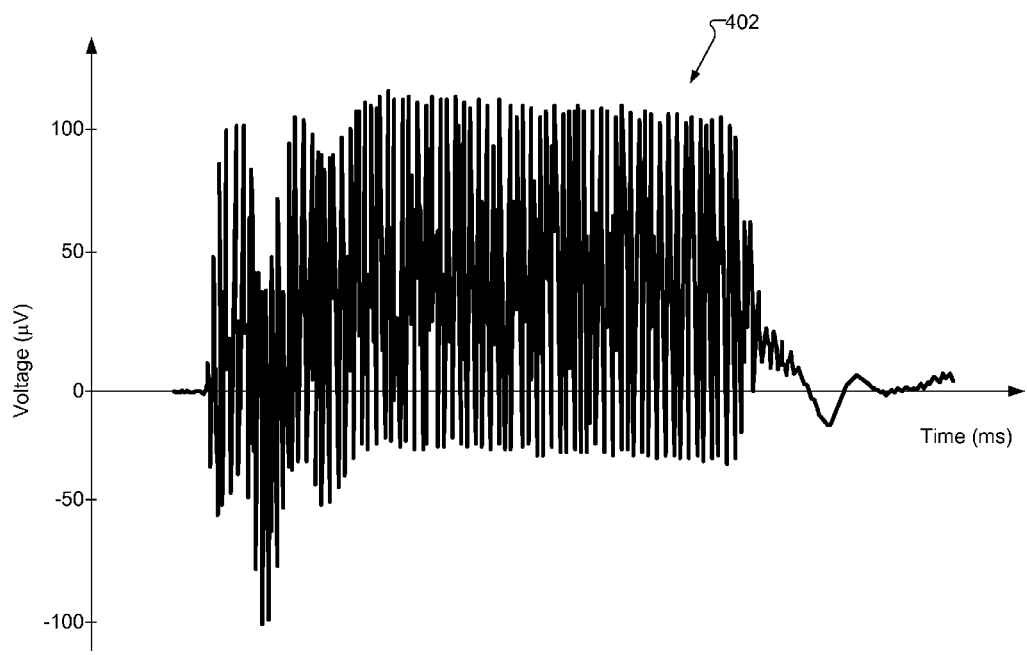
FIGS. 4A-4C show an exemplary baseline response that may occur in response to application of acoustic stimulation by itself and two possible evoked responses that may occur in response to concurrent application of the same acoustic stimulation together with electrical stimulation according to principles described herein.
Figure 4B:
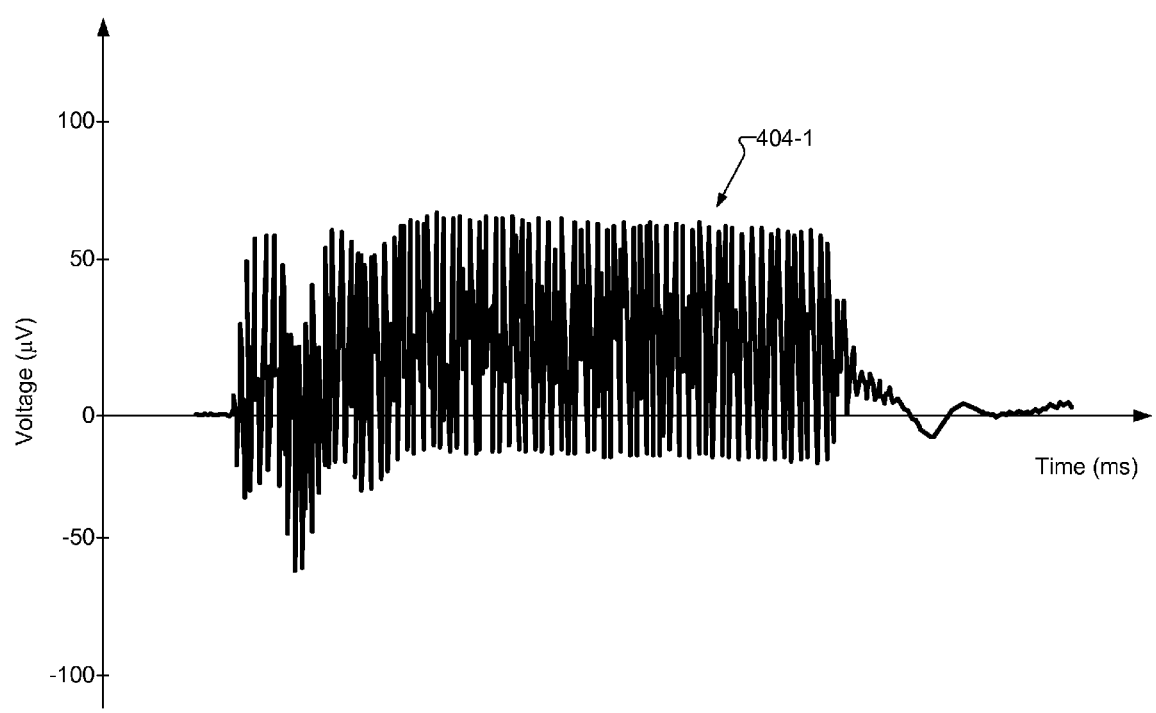
Figure 4C:
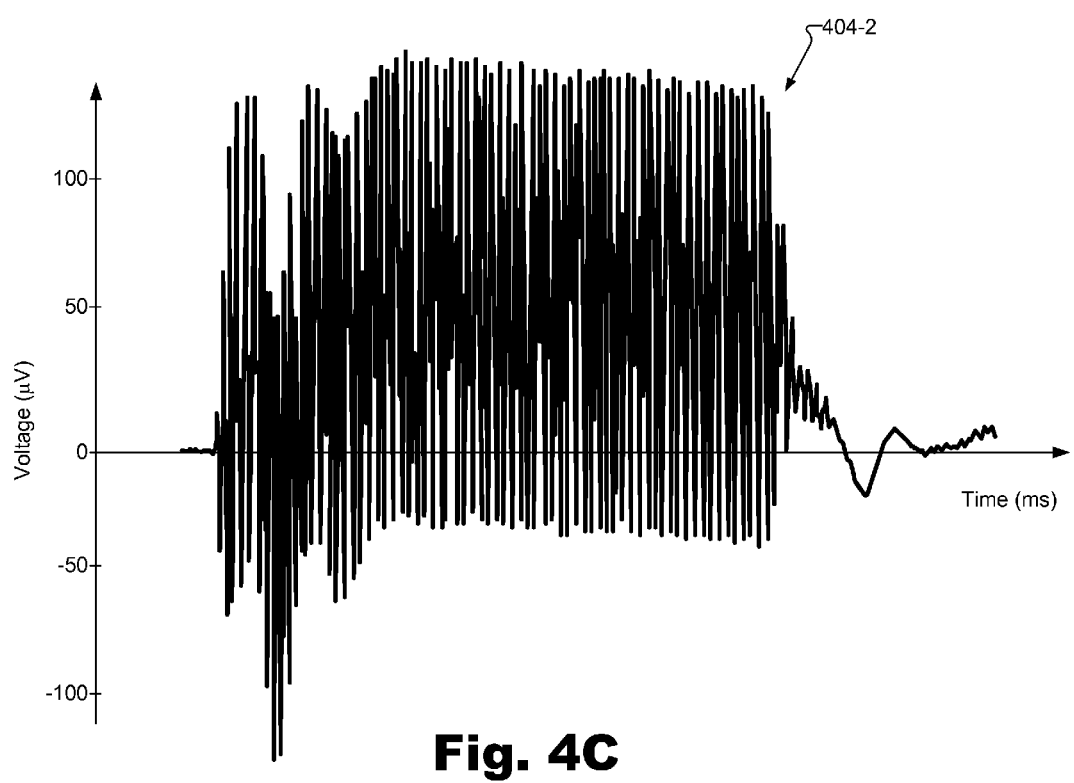

To illustrate, FIG. 4A shows an exemplary baseline response 402 that may occur in response to application of acoustic stimulation by itself. FIGS. 4B and 4C show two possible evoked responses 404-1 and 404-2 that may occur in response to concurrent application of the same acoustic stimulation together with electrical stimulation. As shown in FIG. 4B, evoked response 404-1 is less than baseline response 402 (i.e., evoked response 404-1 has an amplitude that is less than the amplitude of baseline response 402). Hence, if concurrent application of the acoustic and electrical stimulation results in an evoked response similar to evoked response 404-1 (i.e., if the evoked response is less than baseline response 402), fitting facility 304 may determine that the electrical stimulation has a suppressive interactive effect on the acoustic stimulation. Conversely, as shown in FIG. 4C, evoked response 404-2 is greater than baseline response 402 (i.e., evoked response 404-2 has an amplitude that is greater than the amplitude of baseline response 402). Hence, if concurrent application of the acoustic and electrical stimulation results in an evoked response similar to evoked response 404-2 (i.e., if the evoked response is greater than baseline response 402), fitting facility 304 may determine that the electrical stimulation has an enhancing interactive effect on the acoustic stimulation.

A baseline response (e.g., baseline response 402) may be measured or determined by fitting facility 304 in any suitable manner. For example, fitting facility 304 may measure a baseline response that occurs in response to application of acoustic stimulation by directing an EAS system to apply the acoustic stimulation, recording an evoked response that occurs in response to the application of the acoustic stimulation, designating the evoked response that occurs in response to the application of the acoustic stimulation as the baseline response, and storing data representative of the baseline response. The acoustic stimulation used to elicit the baseline response may include any suitable type of acoustic stimulation as may serve a particular implementation. For example, the acoustic stimulation used to elicit the baseline response may include a relatively low frequency tone burst (e.g., a 125 Hz tone burst).

An evoked response may be recorded in any suitable manner using any suitable combination of recording electrodes. For example, an intracochlear hair-cell response (cochlear microphonics) may be recorded using one or more electrodes positioned within the cochlea (e.g., one or more of electrodes 108), one or more electrodes positioned within the round window, and/or one or more electrodes positioned at any other suitable location relatively near the cochlea. Likewise, an auditory nerve response and/or a compound action potential may be recorded using one or more electrodes positioned within or near the cochlea. It will be recognized that the electrodes used to record the evoked response may be disposed on a lead that has been inserted into the cochlea (e.g., electrode array 106) and/or on a fly lead that has been positioned at any other suitable location within the patient.

An evoked response may be recorded in any suitable manner using any suitable combination of recording electrodes. For example, an intracochlear hair-cell response may be recorded in accordance with one or more cochlear microphonics techniques using one or more electrodes positioned within the cochlea (e.g., one or more of electrodes 108), one or more electrodes positioned within the round window, and/or one or more electrodes positioned at any other suitable location relatively near the cochlea. Likewise, an auditory nerve response and/or a compound action potential may be recorded using one or more electrodes positioned within or near the cochlea. It will be recognized that the electrodes used to record the evoked response may be disposed on an electrode array that has been inserted into the cochlea (e.g., electrode array 106) and/or on a fly electrode array that has been positioned at any other suitable location within the patient.

In some examples, one or more electrodes located external to the patient may be used to record an evoked response. For example, a brainstem response may be recorded using one or more non-invasive electrodes that have been affixed externally to the head of the patient.

Additionally or alternatively, fitting facility 304 may determine an interactive effect that the electrical stimulation has on the acoustic stimulation based on subjective feedback provided by the patient. For example, fitting facility 304 may direct the EAS system to first present only the acoustic stimulation to the patient. Immediately thereafter, fitting facility 304 may direct the EAS system to concurrently present the same acoustic stimulation together with electrical stimulation to the patient. A clinician may ask the patient to compare the two types of stimulation (i.e., the acoustic stimulation by itself versus acoustic stimulation together with electrical stimulation). In response, the patient may indicate that one type of stimulation was louder, clearer, or otherwise different than the other type of stimulation. In response to this subjective feedback, the clinician may provide data representative of the interactive effect that the electrical stimulation has on the acoustic stimulation to fitting facility 304 (e.g., by way of one or more graphical user interfaces provided by fitting facility 304).

As another example, fitting facility 304 may determine an interactive effect that the electrical stimulation has on the acoustic stimulation by performing a spectral ripple test with respect to the ear associated with the EAS system. During an exemplary spectral ripple test, a spectral ripple test score is generated for the ear that indicates the smallest spectral contrast of a spectrally modulated stimulus that the ear is capable of detecting. Exemplary spectral ripple tests that may be used in accordance with the methods and systems described herein are described more fully in U.S. Pat. No. 8,027,734, which patent is incorporated herein by reference in its entirety.

To illustrate, a spectral ripple test may be performed by determining the smallest spectral contrast of a spectrally modulated acoustic stimulus that the ear is capable of detecting with and without the concurrent application of an electrical stimulus. If the spectral ripple test score improves in the presence of the electrical stimulus, fitting facility 304 may determine that the electrical stimulation has an enhancing interactive effect on the acoustic stimulation. Conversely, if the spectral ripple test score decreases in the presence of the electrical stimulus, fitting facility 304 may determine that the electrical stimulation has a suppressive interactive effect on the acoustic stimulation. If the spectral ripple test score does not change in the presence of the electrical stimulus, fitting facility 304 may determine that the electrical stimulation does not have either a suppressive or an enhancing interactive effect on the acoustic stimulation.

Once fitting facility 304 has determined the type of interactive effect that the electrical stimulation has on the acoustic stimulation (i.e., whether the electrical stimulation has a suppressive interactive effect, an enhancing interactive effect, or no interactive effect on the acoustic stimulation), fitting facility 304 may set one or more electrical stimulation control parameters governing an operation of the EAS system based on the determined interactive effect.

To illustrate, fitting facility 304 may determine that the electrical stimulation provided by way of the electrode has a suppressive interactive effect on the acoustic stimulation provided by way of the loudspeaker. In response, fitting facility 304 may direct (e.g., by programming the EAS system) the EAS system to use, during a stimulation session subsequent to the fitting session, a stimulation strategy that steers a current field produced by stimulation of the electrode away from intracochlear acoustic responders within the patient that are associated with the acoustic stimulation. As used herein, a "stimulation session" refers to a period of time in which the EAS system operates "normally" by processing acoustic content (e.g., speech and/or other sound) presented to the patient and representing the acoustic content to the patient in the form of electrical and/or acoustic stimulation.

Figure 5A:
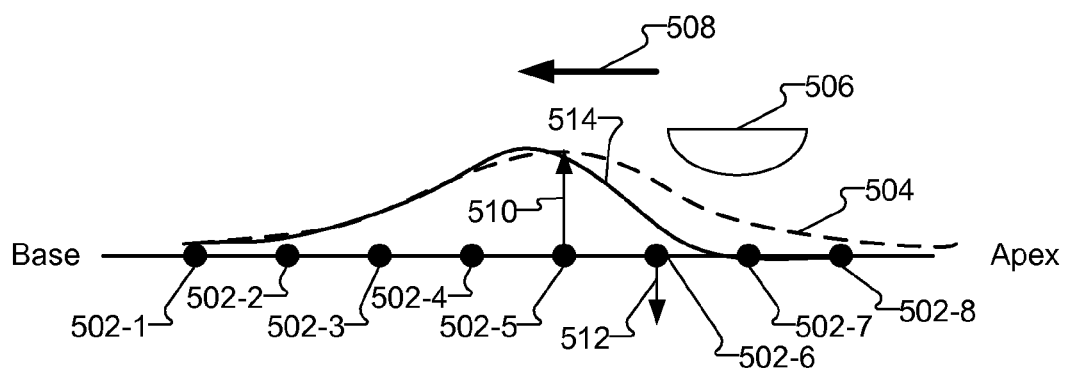
FIGS. 5A-5B show exemplary scenarios in which electrical stimulation provided by way of an electrode included in an EAS system has a suppressive interactive effect on acoustic stimulation provided by way of a loudspeaker included in the EAS system according to principles described herein.

FIG. 5A shows an exemplary scenario in which electrical stimulation provided by way of an electrode included in an EAS system has a suppressive interactive effect on acoustic stimulation provided by way of a loudspeaker included in the EAS system. As shown, a plurality of electrodes 502 (e.g., electrodes 502-1 through 502-8) may be disposed within a cochlea of a patient. The electrodes 502 may be positioned at various locations in between the base and apex of the cochlea. In the example of FIG. 5A, a first electrode located to the right of a second electrode is more apically located within the cochlea than the second electrode. As an example, electrode 502-6 is more apically located within the cochlea than electrode 502-5. Likewise, a first electrode located to the left of a second electrode is more basally located within the cochlea than the second electrode. As an example, electrode 502-4 is more basally located within the cochlea than electrode 502-5.

In the example of FIG. 5A, stimulation management facility 302 may concurrently apply, during a fitting session, electrical stimulation by way of electrode 502-5 and acoustic stimulation by way of the loudspeaker. The electrical stimulation may include, for example, monopolar stimulation and may result in a relatively broad current field 504 (which is represented by dashed lines in FIG. 5A for illustrative purposes). The acoustic stimulation may be detected and responded to by acoustic responders 506, which may result in an evoked response that may be detected in any of the ways described herein. Acoustic responders 506 may be identified in any suitable manner. For example, fitting facility 304 may identify one or more acoustic frequencies that the patient can perceive in response to the acoustic stimulation and designate a portion of the cochlea that corresponds to the identified one or more acoustic frequencies as the acoustic responders.

In the example of FIG. 5A, the electrical stimulation has a suppressive interactive effect on acoustic stimulation. Hence, fitting facility 304 may direct the EAS system to use, during a stimulation session subsequent to the fitting session, a stimulation strategy that steers a current field produced by stimulation of electrode 502-5 away from (i.e., in a direction represented by arrow 508) acoustic responders 506. In some examples, such a strategy may be referred to as "phantom electrode stimulation." In phantom electrode stimulation, the EAS system represents acoustic content presented to the patient during a stimulation session by concurrently applying a main current having a first polarity to the electrode and compensating current having a second polarity opposite the first polarity to one or more additional electrodes that are closer (e.g., physically closer) acoustic responders than the electrode. As will be described below, the compensating current steers the current field produced by the main current away from the one or more additional electrodes (and hence, the acoustic responders). Exemplary phantom electrode stimulation strategies are described in U.S. Pat. No. 8,165,690, which patent is incorporated herein by reference in its entirety.

To illustrate, reference is again made to FIG. 5A. In order to represent acoustic content (e.g., speech and/or other sound) presented to the patient and that is associated with electrode 502-5 (e.g., that has a frequency that is mapped to electrode 502-5), the EAS system may apply main current 510 to electrode 502-5. The main current 510 is configured to represent the acoustic content. Compensating current 512 may also be concurrently applied to electrode 502-6, which, as shown, is more apically located within the cochlea than electrode 502-5. Compensating current 512 has a polarity that is opposite that of main current 510. For example, in the example of FIG. 5A, main current 510 has a positive polarity (as indicated by the upward direction of the arrow used to represent main current 510) and compensating current 512 has a negative polarity (as indicated by the downward direction of the arrow used to represent compensating current 512). Compensating current 512 is also lower in magnitude than main current 510.

Because electrode 502-6 is more apically located than electrode 502-5, and because compensating current 512 is opposite in polarity than main current 510, compensating current 512 steers the current field produced by main current 510 towards the base. This steered current field is represented in FIG. 5A by a solid line 514. As shown, steered current field 514 is further away from acoustic responders 506 than the current field 504 produced by monopolar stimulation of electrode 502-5. In this manner, the suppressive interactive effect of main current 510 on acoustic stimulation may be reduced.

In the example of FIG. 5A, the compensating current 512 is applied to an electrode (i.e., electrode 502-6) that is adjacent to the electrode (i.e., electrode 502-5) to which the main current 510 is applied. As used herein, "adjacent" electrodes do not have any intervening electrodes disposed therebetween. It will be recognized that compensating current 512 may alternatively be applied to one or more other electrodes (e.g., electrodes 502-7 and/or 502-8) that are more apically located than electrode 502-6.

Figure 5B:
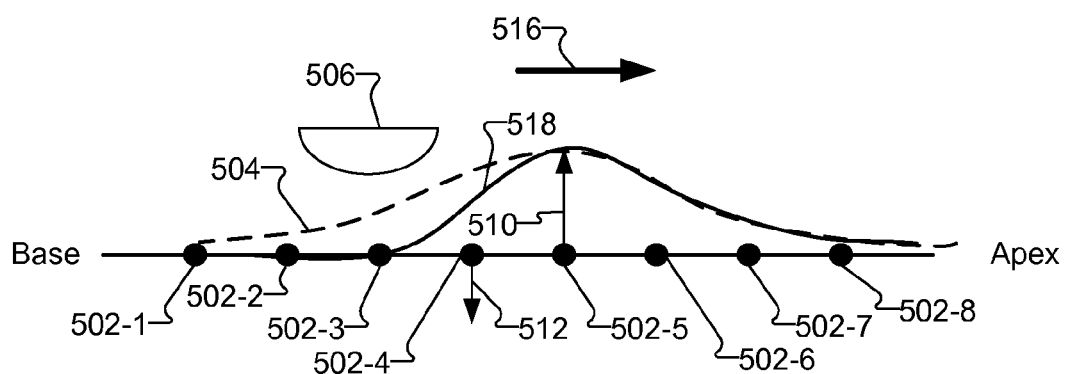

FIG. 5B shows another exemplary scenario in which electrical stimulation provided by way of an electrode included in an EAS system has a suppressive interactive effect on acoustic stimulation provided by way of a loudspeaker included in the EAS system. FIG. 5B is similar to FIG. 5A, except that in FIG. 5B the acoustic responders 506 are more basally located than electrode 502-5 to which the main current 510 is applied. In this scenario, a stimulation strategy that steers the current field produced by stimulation of electrode 502-5 towards the acoustic responders 506 (which direction is represented by arrow 516) may be employed by the EAS system (e.g., in accordance with programming instructions provided by fitting system 300) in order to reduce the suppressive interactive effect of main current 510 on acoustic stimulation.

For example, as shown in FIG. 5B, main current 510 is applied to electrode 502-5, as it was in the example of FIG. 5A. However, because acoustic responders 506 are more basally located than electrode 502-5, compensating current 512 is applied to electrode 502-4, which is closer to acoustic responder 506 than electrode 502-5. By so doing, the electric field 518 produced by main current 510 is steered away from acoustic responders 506 towards the apex.

Alternatively, fitting facility 304 may determine that the electrical stimulation provided by way of the electrode has an enhancing interactive effect on the acoustic stimulation provided by way of the loudspeaker. In response, fitting facility 304 may direct the EAS system to use, during a stimulation session subsequent to the fitting session, a stimulation strategy that steers a current field produced by stimulation of the electrode towards intracochlear acoustic responders within the patient that are associated with the acoustic stimulation.

Figure 6A:
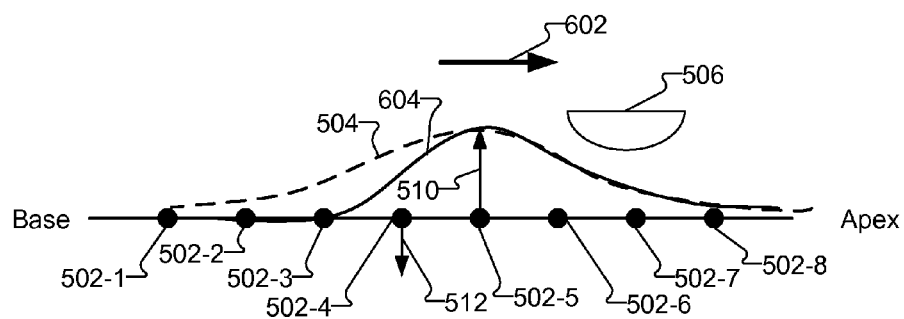
FIGS. 6A-6B show exemplary scenarios in which electrical stimulation provided by way of an electrode included in an EAS system has an enhancing interactive effect on acoustic stimulation provided by way of a loudspeaker included in the EAS system according to principles described herein.

To illustrate, FIG. 6A shows an exemplary scenario in which electrical stimulation provided by way of an electrode included in an EAS system has an enhancing interactive effect on acoustic stimulation provided by way of a loudspeaker included in the EAS system. FIG. 6A is similar to FIG. 5A in that the acoustic responders 506 are more apically located than electrode 502-5 to which the main current 510 is applied. Hence, in order to steer the current field produced by stimulation of electrode 502-5 towards the acoustic responders 506 (which direction is represented by arrow 602), EAS system may apply compensating current 512 to electrode 502-4, which is further away from acoustic responders 506 than electrode 502-4. The steered current field is represented in FIG. 6A by a solid line 604. As shown, steered current field 604 is closer to acoustic responders 506 than the current field 504 produced by monopolar stimulation of electrode 502-5. In this manner, the enhancing interactive effect of main current 510 on acoustic stimulation may be increased.

Figure 6B:
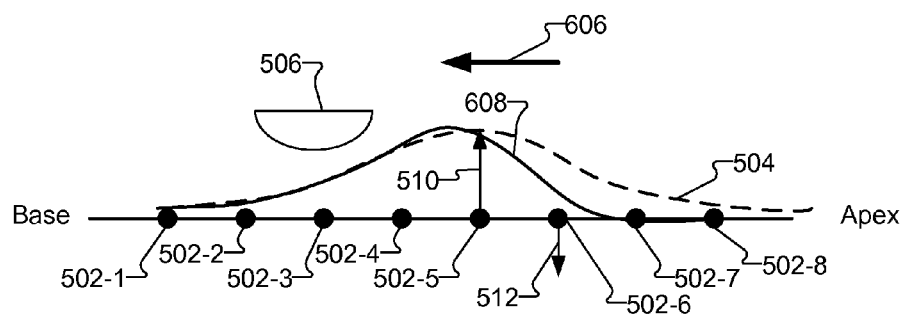

FIG. 6B shows another exemplary scenario in which electrical stimulation provided by way of an electrode included in an EAS system has an enhancing interactive effect on acoustic stimulation provided by way of a loudspeaker included in the EAS system. FIG. 6B is similar to FIG. 6A, except that in FIG. 6B the acoustic responders 506 are more basally located than electrode 502-5 to which the main current 510 is applied. In this scenario, a stimulation strategy that steers the current field produced by stimulation of electrode 502-5 towards the acoustic responders 506 (which direction is represented by arrow 606) may be employed by the EAS system (e.g., in accordance with programming instructions provided by fitting system 300) in order to increase the enhancing interactive effect of main current 510 on acoustic stimulation.

For example, as shown in FIG. 6B, main current 510 is applied to electrode 502-5, as it was in the example of FIG. 6A. However, because acoustic responders 506 are more basally located than electrode 502-5, compensating current 512 is applied to electrode 502-6, which is further away from acoustic responder 506 than electrode 502-5. By so doing, the electric field 608 produced by main current 510 is steered towards acoustic responders 506.

In some examples, in response to fitting facility 304 determining that the electrical stimulation has a suppressive interactive effect on the acoustic stimulation, fitting facility 304 may adjust one or more properties of the electrical stimulation in a manner that reduces the suppressive interactive effect of the electrical stimulation on the acoustic stimulation. For example, the intensity level, pulse width, and/or rate of the electrical stimulation may be adjusted until the suppressive interactive effect is minimized. It will be recognized that any other characteristic of the electrical stimulation may be adjusted in order to minimize the suppressive interactive effect of the electrical stimulation on the acoustic stimulation as may serve a particular implementation. Fitting facility 304 may then direct the EAS system to limit the type of electrical stimulation provided by way of the electrode subsequent to the fitting session to that defined by the adjusted one or more parameters.

In some alternative examples, fitting facility 304 may designate the electrode through which the suppressive electrical stimulation is applied as being disabled subsequent to the fitting session. In this manner, electrical stimulation will not be applied by way of the designated electrode during normal operation of the EAS system (i.e., while the EAS system is operating in a non-fitting mode). Rather, acoustic stimulation will be used to represent sound within the frequency range associated with the electrode.

In some examples, fitting facility 304 may first adjust one or more properties of the electrical stimulation provided by way of a particular electrode in an attempt to reduce (e.g., minimize or eliminate) the suppressive interactive effect that the electrical stimulation has on the acoustic stimulation. If fitting facility 304 determines that adjustment of the one or more properties of the electrical stimulation does not satisfactorily reduce the suppressive interactive effect of the electrical stimulation on the acoustic stimulation, fitting facility 304 may then designate the electrode as being disabled subsequent to the fitting session.

To illustrate, fitting facility 304 may determine that electrical stimulation provided by way of the most apical electrode (i.e., the electrode that is most apically located within an array of electrodes) has a suppressive interactive effect on the acoustic stimulation. In response, fitting facility 304 may adjust one or more properties of the electrical stimulation provided by way of the most apical electrode. If this adjustment does not reduce the suppressive interactive effect of the electrical stimulation on the acoustic stimulation (which may be determined by recording one or more additional evoked responses after the one or more properties have been adjusted), fitting facility 304 may designate the most apical electrode as being disabled subsequent to the fitting session.

In some examples, fitting facility 304 may determine that the electrical stimulation delivered by way of a particular electrode has an enhancing interactive effect on the acoustic stimulation. In response, fitting facility 304 may designate the electrode as an enhancing electrode through which enhancing electrical stimulation is to be applied subsequent to the fitting session.

As used herein, "enhancing stimulation" refers to any type of electrical stimulation configured to enhance acoustic stimulation. For example, enhancing stimulation may include sub-threshold electrical stimulation (i.e., electrical stimulation that has a stimulation level that is less than a threshold level required for the patient to perceive the electrical stimulation). Concurrent application of sub-threshold electrical stimulation by way of an electrode together with acoustic stimulation may enhance the acoustic stimulation in a variety of ways. For example, the sub-threshold electrical stimulation may lower an acoustic detection threshold of the patient. As used herein, an "acoustic detection threshold" of a patient refers to a sound level of acoustic stimulation that is required for the patient to detect the acoustic stimulation. Hence, the sub-threshold electrical stimulation may make it easier for the patient to detect the acoustic stimulation. Sub-threshold electrical stimulation may additionally or alternatively serve to maintain patency (i.e., inhibit neuropathy) of hearing nerve cells located in the region of the cochlea that is associated with the electrode.

The EAS system may apply enhancing stimulation by way of the designated enhancing electrode in any suitable way. For example, EAS device 102 may direct cochlear implant 104 to apply steady-state electrical stimulation by way of the designated electrode during the application of the acoustic stimulation. As another example, EAS device 102 may direct cochlear implant 104 to apply sporadic electrical stimulation by way of the designated electrode during the application of the acoustic stimulation. As another example, EAS device 102 may direct cochlear implant 104 to apply periodic electrical stimulation by way of the designated electrode during the application of the acoustic stimulation. Each type of enhancing stimulation may include monopolar, bipolar, multipolar, and/or any other type of electrical stimulation as may serve a particular implementation.

In some examples, fitting facility 304 may determine that the electrical stimulation delivered by way of a particular electrode does not have either a suppressive or enhancing interactive effect on the acoustic stimulation. In this case, fitting facility 304 may designate the electrode as an electrode through which standard electrical stimulation is to be applied subsequent to the fitting session. As used herein, "standard electrical stimulation" refers to electrical stimulation used to represent audio content presented to the patient. Hence, electrical stimulation may be applied by way of the designated electrode to represent audio content having a frequency included within a range of frequencies associated with that electrode.

In some examples, fitting facility 304 may determine an interactive effect that the acoustic stimulation has on the electrical stimulation and set one or more acoustic stimulation control parameters governing an operation of the EAS system based on the determined interactive effect. As used herein, "acoustic stimulation control parameters" refer to control parameters that govern a manner in which an EAS system applies acoustic stimulation to a patient.

Fitting facility 304 may determine an interactive effect that the acoustic stimulation has on the electrical stimulation in any suitable manner. To illustrate, fitting facility 304 may determine an interactive effect that the acoustic stimulation has on the electrical stimulation by measuring an evoked response that occurs in response to the concurrent application of the acoustic stimulation and the electrical stimulation and comparing the evoked response to a baseline response that occurs in response to an application of the electrical stimulation by itself.

For example, if the evoked response is greater than the baseline response, fitting facility 304 may determine that the acoustic stimulation has an enhancing interactive effect on the electrical stimulation. Conversely, if the evoked response is less than the baseline response, fitting facility 304 may determine that the acoustic stimulation has a suppressive interactive effect on the electrical stimulation. If the evoked response is substantially equal to the baseline response, fitting facility 304 may determine that the acoustic stimulation has substantially no interactive effect on the electrical stimulation. It will be recognized that the evoked response and baseline response may be generated and measured in a manner that is similar to that described above in connection with FIG. 4.

In some examples, fitting facility 304 may determine an interactive effect that the acoustic stimulation has on the electrical stimulation based on subjective feedback provided by the patient. This may be performed in a similar manner as that described above.

Once fitting facility 304 has determined the type of interactive effect that the acoustic stimulation has on the electrical stimulation (i.e., whether the acoustic stimulation has a suppressive interactive effect, an enhancing interactive effect, or no interactive effect on the electrical stimulation), fitting facility 304 may set one or more acoustic stimulation control parameters governing an operation of the EAS system based on the determined interactive effect.

To illustrate, fitting facility 304 may determine that the acoustic stimulation has a suppressive interactive effect on the electrical stimulation. In response, fitting facility 304 may adjust one or more properties of the acoustic stimulation in a manner that reduces the suppressive interactive effect of the acoustic stimulation on the electrical stimulation. For example, the intensity level, duration, and/or frequency of the acoustic stimulation may be adjusted until the suppressive interactive effect is minimized. It will be recognized that any other characteristic of the acoustic stimulation may be adjusted in order to minimize the suppressive interactive effect of the acoustic stimulation on the electrical stimulation as may serve a particular implementation.

In some examples, if the adjustment of the one or more properties of the acoustic stimulation does not result in a satisfactory reduction in the suppressive interactive effect, fitting facility 304 may direct the EAS system to not apply the acoustic stimulation while the electrical stimulation is delivered subsequent to the fitting session (i.e., during a normal operation of the EAS system).

As another example, fitting facility 304 may determine that the acoustic stimulation has an enhancing interactive effect on the electrical stimulation. In response, fitting facility 304 may direct the EAS system to apply the acoustic stimulation while the electrical stimulation is delivered subsequent to the fitting session (i.e., during a normal operation of the EAS system).

In some examples, fitting facility 304 may determine that the acoustic stimulation does not have either a suppressive or enhancing interactive effect on the electrical stimulation. In this case, fitting facility 304 directs the EAS system to not apply the acoustic stimulation while the electrical stimulation is delivered subsequent to the fitting session (i.e., during a normal operation of the EAS system). This may allow the EAS system to conserve power during normal operation.

While the functions of determining an interactive effect that the electrical stimulation has on the acoustic stimulation and determining an interactive effect that the acoustic stimulation has on the electrical stimulation have been described separately, it will be recognized that fitting facility 304 may concurrently determine the interactive effect that each type of stimulation has on the other. Fitting facility 304 may then set one or more electrical and/or acoustic stimulation parameters based on the determined interactive effect.

In some examples, fitting facility 304 may determine an optimal crossover frequency associated with the acoustic stimulation and the electrical stimulation based on the detected interaction between the acoustic stimulation and the electrical stimulation. As used herein, a "crossover frequency" refers to a boundary frequency that separates frequencies represented to the patient by acoustic stimulation and frequencies represented to the patient by electrical stimulation. For example, fitting facility 304 may determine that acoustic stimulation evokes a robust hair cell and neural responses until 450 Hz, the most apical electrode can start providing stimulation around that frequency, provided there is no suppression of the acoustic response. In case suppression is observed, the fitting system may adjust one or more properties of the electrical stimulation. If a satisfactory reduction in the suppressive interactive effect is realized by the adjustment of the one or more properties of the electrical stimulation, the fitting system may designate the electrode as an electrode through which standard electrical stimulation is to be applied subsequent to the fitting session. However, if a satisfactory reduction in a suppressive interactive effect is not realized by the adjustment of the one or more properties of the electrical stimulation, the fitting system may disable the electrode. The next electrode is then selected to provide stimulation around 450 Hz provided there are no suppressive effects observed again. In addition, other stimulation properties (such as Phantom stimulation) could be applied in an attempt to decrease the amount of interaction. Various other properties (e.g., intensity levels at the crossover frequency, a slope of one or more filters at the crossover frequency, and/or other EAS parameters used to fit an EAS system to a patient) associated with the crossover frequency may also be determined based on the detected interaction.

In some examples, if the electrical stimulation has a suppressive interactive effect on the acoustic stimulation only above a certain frequency threshold (e.g., 300 Hz), then acoustic stimulation may be used for frequencies below the frequency threshold and electric stimulation may be used for frequencies above the frequency threshold.

Additionally or alternatively, if suppressive interaction between electrical and acoustic stimulation is observed in a certain acoustic range (e.g., in the high frequencies) that cannot be avoided, electrical stimulation (to the exclusion of acoustic stimulation) may be used for the acoustic range.

Fitting system 300 may be implemented by one or more components of EAS system 100. For example, fitting system 300 may be implemented entirely by EAS device 102. To illustrate, EAS device 102 may periodically analyze an interaction that occurs between acoustic and electrical stimulation and adjust one or more control parameters accordingly. In this case, the term "fitting session" may refer to the period of time during which EAS device 102 performs the analysis.

Figure 7:
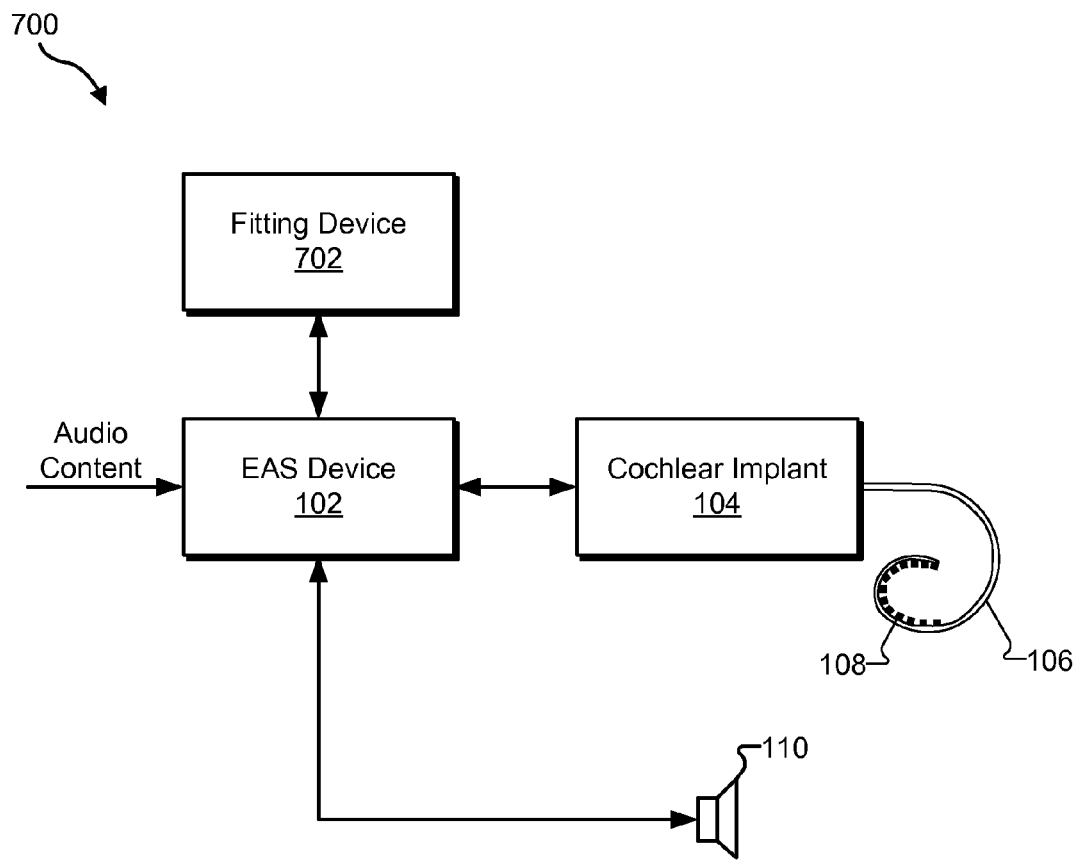
FIG. 7 shows an exemplary configuration in which the fitting system of FIG. 3 is at least partially implemented by a fitting device communicatively coupled to an EAS device according to principles described herein.

Alternatively, fitting system 300 may be at least partially implemented by a fitting device selectively and communicatively coupled to EAS device 102. To illustrate, FIG. 7 shows an exemplary configuration 700 in which fitting system 300 is at least partially implemented by a fitting device 702 communicatively coupled to EAS device 102. Fitting device 702 may implemented by any suitable combination of computing and communication devices including, but not limited to, a fitting station, a personal computer, a laptop computer, a handheld device, a mobile device (e.g., a mobile phone), and/or any other suitable component as may serve a particular implementation. In some examples, fitting device 702 may provide one or more graphical user interfaces ("GUIs") with which a clinician or other user may interface in order to fit EAS system 100 to the patient.

Figure 8:
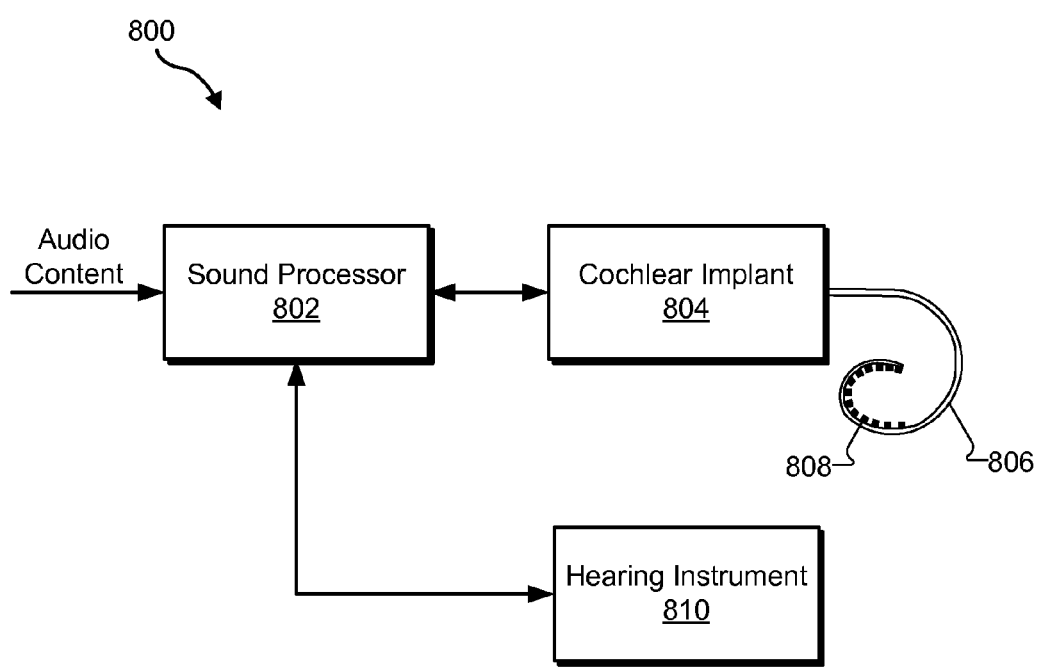
FIG. 8 illustrates an exemplary bimodal cochlear implant system according to principles described herein.

In some examples, fitting system 300 may be used to understand and evaluate interactions between acoustic and electrical stimulation in a bimodal cochlear implant system. FIG. 8 illustrates an exemplary bimodal cochlear implant system 800 that may be used by a bimodal cochlear implant patient (i.e., a patient fitted with a cochlear implant for one ear and an acoustic hearing instrument for the other ear). As shown, bimodal cochlear implant system 800 may include a sound processor 802, a cochlear implant 804, and an electrode array 806 having a plurality of electrodes 808 disposed thereon. Bimodal cochlear implant system 800 may also include a hearing instrument 810 communicatively coupled to sound processor 802. Hearing instrument 810 may include any type of acoustic hearing aid as may serve a particular implementation.

Cochlear implant 804 may be used to apply electrical stimulation to one of the ears of the patient and hearing instrument 810 may be used to apply acoustic stimulation to the other ear of the patient. Both cochlear implant 804 and hearing instrument 810 may be controlled by sound processor 802, which may receive and process audio content.

In some examples, fitting system 300 may be used to detect and evaluate interactions between the ipsilateral (same ear) or contralateral (opposite ear) acoustic stimulation provided by hearing instrument 810 and the electrical stimulation provided by cochlear implant 804. To this end, fitting system 300 may be at least partially implemented by sound processor 802 and/or a fitting device (which may be similar to fitting device 702) selectively and communicatively coupled to sound processor 802.

Figure 9:
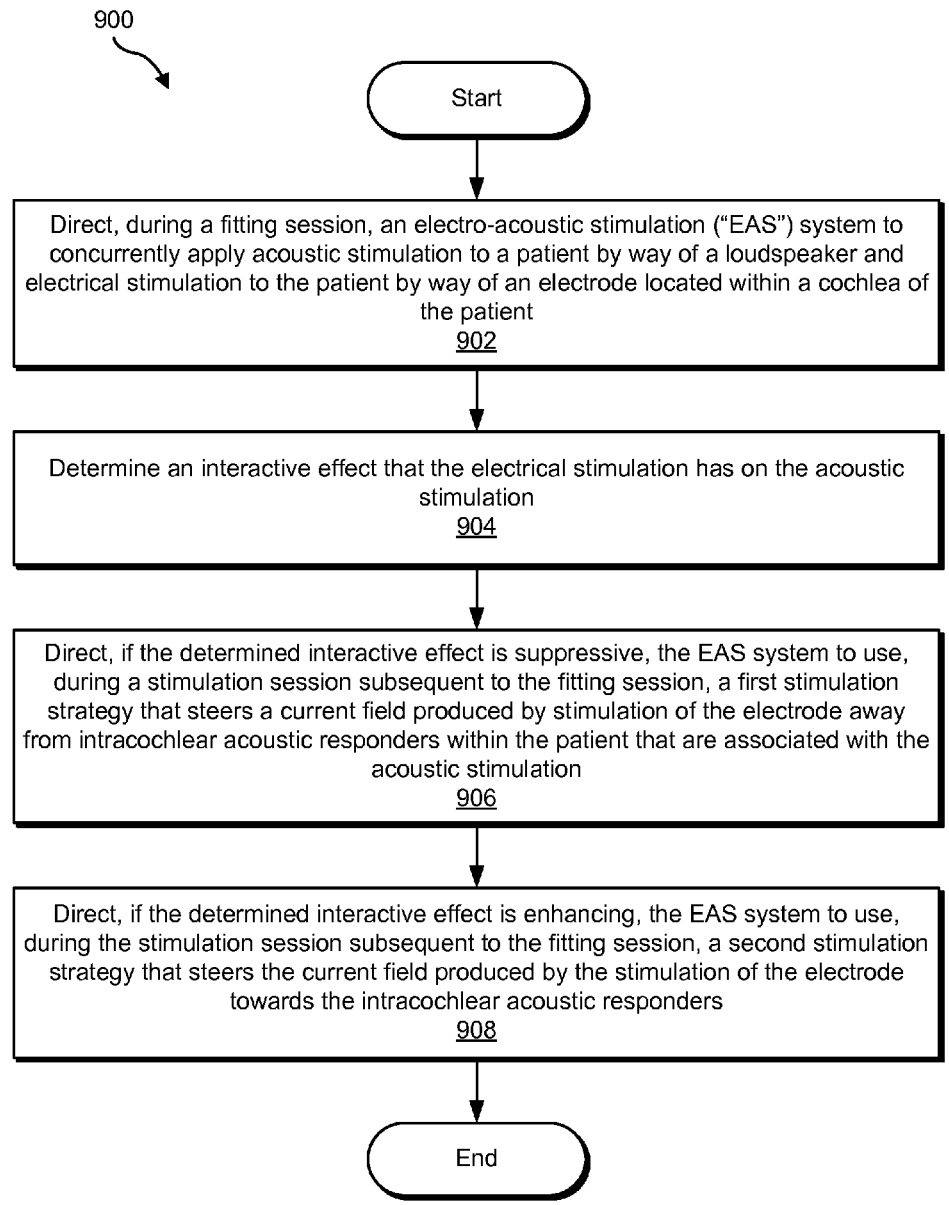
FIG. 9 illustrates an exemplary method of fitting an EAS system to a patient according to principles described herein.

FIG. 9 illustrates an exemplary method 900 of fitting an EAS system to a patient. While FIG. 9 illustrates exemplary steps according to one embodiment, other embodiments may omit, add to, reorder, and/or modify any of the steps shown in FIG. 9. One or more of the steps shown in FIG. 9 may be performed by fitting system 300 and/or any implementation thereof.

In step 902, a fitting system directs, during a fitting session, an EAS system to concurrently apply acoustic stimulation to a patient by way of a loudspeaker and electrical stimulation to the patient by way of an electrode located within a cochlea of the patient. Step 902 may be performed in any of the ways described herein.

In step 904, the fitting system determines, during the fitting session, an interactive effect that the electrical stimulation has on the acoustic stimulation. Step 904 may be performed in any of the ways described herein.

In step 906, the fitting system directs, if the determined interactive effect is suppressive, the EAS system to use, during a stimulation session subsequent to the fitting session, a first stimulation strategy that steers a current field produced by stimulation of the electrode away from intracochlear acoustic responders within the patient that are associated with the acoustic stimulation. Step 906 may be performed in any of the ways described herein.

In step 908, the fitting system directs, if the determined interactive effect is enhancing, the EAS system to use, during the stimulation session subsequent to the fitting session, a second stimulation strategy that steers the current field produced by the stimulation of the electrode towards the intracochlear acoustic responders. Step 908 may be performed in any of the ways described herein.

In certain embodiments, one or more of the processes described herein may be implemented at least in part as instructions embodied in a non-transitory computer-readable medium and executable by one or more computing devices.

In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 10:
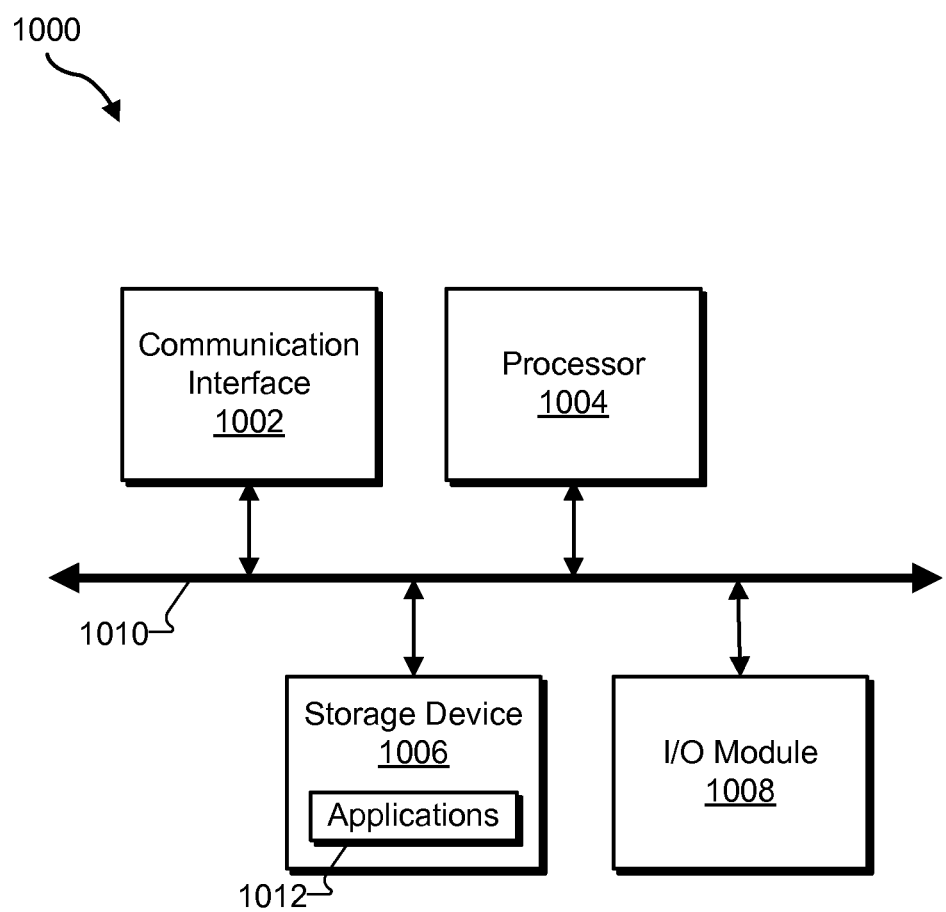
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data or interpreting, executing, and/or directing execution of one or more of the instructions, processes, and/or operations described herein. Processor 1004 may direct execution of operations in accordance with one or more applications 1012 or other computer-executable instructions such as may be stored in storage device 1006 or another computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct processor 1004 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
  a stimulation management facility that directs, during a fitting session, an electro-acoustic stimulation ("EAS") system to concurrently apply acoustic stimulation to a patient by way of a loudspeaker and electrical stimulation to the patient by way of an electrode located within a cochlea of the patient; and
  a fitting facility communicatively coupled to the stimulation management facility and that
    determines an interactive effect that the electrical stimulation has on the acoustic stimulation,
    directs, if the fitting facility determines that the interactive effect is suppressive, the EAS system to use, during a stimulation session subsequent to the fitting session, a first stimulation strategy that steers a current field produced by stimulation of the electrode away from intracochlear acoustic responders within the patient that are associated with the acoustic stimulation, and
    directs, if the fitting facility does not determine that the interactive effect is suppressive, the EAS system to use, during the stimulation session subsequent to the fitting session, a second stimulation strategy that steers the current field produced by the stimulation of the electrode towards the intracochlear acoustic responders.

2. The system of claim 1, wherein, if the determined interactive effect is suppressive, the fitting facility directs the EAS system to use the first stimulation strategy during the stimulation session by directing the EAS system to represent acoustic content associated with the electrode and presented to the patient during the stimulation session by concurrently applying a main current having a first polarity to the electrode and compensating current having a second polarity opposite the first polarity to an additional electrode that is closer to the intracochlear acoustic responders than the electrode.

3. The system of claim 2, wherein the additional electrode is more apically located within the cochlea than the electrode.

4. The system of claim 2, wherein the additional electrode is more basally located within the cochlea than the electrode.

5. The system of claim 1, wherein, if the fitting facility does not determine that the interactive effect is suppressive, the fitting facility directs the EAS system to use the second stimulation strategy during the stimulation session by directing the EAS system to represent acoustic content associated with the electrode and presented to the patient during the stimulation session by concurrently applying a main current having a first polarity to the electrode and compensating current having a second polarity opposite the first polarity to an additional electrode that is further away from the intracochlear acoustic responders than the electrode.

6. The system of claim 5, wherein the additional electrode is more apically located within the cochlea than the electrode.

7. The system of claim 5, wherein the additional electrode is more basally located within the cochlea than the electrode.

8. The system of claim 1, wherein the fitting facility determines the interactive effect that the electrical stimulation has on the acoustic stimulation by:
  recording an evoked response that occurs in response to the concurrent application of the acoustic stimulation and the electrical stimulation; and
  comparing the evoked response to a baseline response that occurs in response to an application of the acoustic stimulation by itself;
  wherein, if the evoked response is less than the baseline response, the fitting facility determines that the interactive effect is suppressive; and
  wherein, if the evoked response is greater than the baseline response, the fitting facility does not determine that the interactive effect is suppressive.

9. The system of claim 8, wherein the evoked response comprises at least one of an intracochlear hair-cell response, a neural response, and an electrocochlear potential.

10. The system of claim 8, wherein the fitting facility measures, prior to the recording of the evoked response that occurs in response to the concurrent application of the acoustic stimulation and the electrical stimulation, the baseline response by:
  directing the EAS system to apply the acoustic stimulation;
  recording an evoked response that occurs in response to the application of the acoustic stimulation; and
  designating the evoked response that occurs in response to the application of the acoustic stimulation as the baseline response.

11. The system of claim 1, wherein the fitting facility determines the interactive effect that the electrical stimulation has on the acoustic stimulation based on subjective feedback provided by the patient.

12. The system of claim 1, wherein the electrical stimulation comprises a pulse train.

13. A system comprising:
  an electro-acoustic stimulation ("EAS") device configured to be located external to a patient;
  a cochlear implant communicatively coupled to the EAS device and configured to be implanted within the patient;
  an electrode array communicatively coupled to the cochlear implant and configured to be located within a cochlea of the patient; and
  a loudspeaker communicatively coupled to the EAS device and configured to be in communication with an ear of the patient;
  wherein the EAS device
    concurrently directs, during a fitting session, the cochlear implant to apply electrical stimulation to the patient by way of an electrode included in the electrode array and the loudspeaker to apply acoustic stimulation to the patient,
    determines an interactive effect that the electrical stimulation has on the acoustic stimulation,
    uses, during a stimulation session subsequent to the fitting session and if the EAS device determines that the interactive effect is suppressive, a first stimulation strategy that steers a current field produced by stimulation of the electrode away from intracochlear acoustic responders within the patient that are associated with the acoustic stimulation, and
    uses, during the stimulation session and if the EAS device does not determine that the interactive effect is suppressive, a second stimulation strategy that steers the current field produced by the stimulation of the electrode towards the intracochlear acoustic responders.

14. The system of claim 13, wherein, if the determined interactive effect is suppressive, the EAS device uses the first stimulation strategy during the stimulation session by directing the cochlear implant to concurrently apply a main current having a first polarity to the electrode and compensating current having a second polarity opposite the first polarity to an additional electrode that is closer to the intracochlear acoustic responders than the electrode.

15. The system of claim 14, wherein the additional electrode is more apically located within the cochlea than the electrode.

16. The system of claim 14, wherein the additional electrode is more basally located within the cochlea than the electrode.

17. The system of claim 13, wherein, if the EAS devices does not determine that the interactive effect is suppressive, the EAS device uses the second stimulation strategy during the stimulation session by directing the cochlear implant to concurrently apply a main current having a first polarity to the electrode and compensating current having a second polarity opposite the first polarity to an additional electrode that is further away from the intracochlear acoustic responders than the electrode.

18. The system of claim 17, wherein the additional electrode is more apically located within the cochlea than the electrode.

19. The system of claim 17, wherein the additional electrode is more basally located within the cochlea than the electrode.

20. A method comprising:
  directing, by a fitting system during a fitting session, an electro-acoustic stimulation ("EAS") system to concurrently apply acoustic stimulation to a patient by way of a loudspeaker and electrical stimulation to the patient by way of an electrode located within a cochlea of the patient;

determining, by the fitting system, an interactive effect that the electrical stimulation has on the acoustic stimulation;

directing, by the fitting system if the fitting facility determines that the interactive effect is suppressive, the EAS system to use, during a stimulation session subsequent to the fitting session, a first stimulation strategy that steers a current field produced by stimulation of the electrode away from intracochlear acoustic responders within the patient that are associated with the acoustic stimulation; and directing, by the fitting system if the fitting facility does not determine that the interactive effect is suppressive, the EAS system to use, during the stimulation session subsequent to the fitting session, a second stimulation strategy that steers the current field produced by the stimulation of the electrode towards the intracochlear acoustic responders.

* * * * *